United States Patent
Kreuder et al.

[11] Patent Number: 5,874,179
[45] Date of Patent: Feb. 23, 1999

[54] NITROGEN-CONTAINING POLYMERS AS ELECTROLUMINESCENT MATERIALS

[75] Inventors: Willi Kreuder, Mainz; Hans-Heinrich Hörhold; Henning Rost, both of Jena, all of Germany

[73] Assignee: Hoechst Aktiengesellschaft, Frankfurt, Germany

[21] Appl. No.: 809,772

[22] PCT Filed: Sep. 28, 1995

[86] PCT No.: PCT/EP95/03836

§ 371 Date: Mar. 28, 1997

§ 102(e) Date: Mar. 28, 1997

[87] PCT Pub. No.: WO96/10598

PCT Pub. Date: Apr. 11, 1996

[30] Foreign Application Priority Data

Sep. 30, 1994 [DE] Germany .................. 44 35 047.3
Feb. 17, 1995 [DE] Germany .................. 195 05 416.4

[51] Int. Cl.$^6$ .................. C08G 10/02; H05B 33/14
[52] U.S. Cl. .................. 428/690; 313/504; 313/506; 428/917; 528/230; 528/247; 528/248; 528/249; 528/266; 528/269
[58] Field of Search .................. 528/230, 247, 528/248, 249, 266, 269; 428/690, 917; 313/504, 506

[56] References Cited

U.S. PATENT DOCUMENTS 3,418,261 12/1968 Idelson et al. .
4,952,667 8/1990 Shikatani et al. .................. 528/230
5,227,252 7/1993 Murayama et al. .

FOREIGN PATENT DOCUMENTS 0 295 084 12/1988 European Pat. Off. .
WO 90/13148 11/1990 WIPO .

OTHER PUBLICATIONS

*Chem. Abstracts,* vol. 112, No. 18 (1990), p. 64.

*Primary Examiner*—John M. Cooney, Jr.
*Attorney, Agent, or Firm*—Frommer Lawrence & Haug LLP

[57] ABSTRACT

The invention relates to nitrogen-containing polymers containing structural units of formula (I),

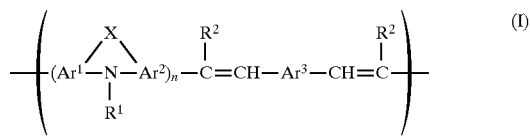

where the symbols and indices have the following meanings:

$Ar^1$, $Ar^2$, $Ar^3$ are, identically or differently, mono- and/or polynuclear and/or condensed aryl and/or heteroaryl groups which may or may not be linked via one or more bridges carbon atoms, which may or may not be substituted;

X is a single bond, —O—, —S—, —SO—, —SO$_2$, NR$^3$, —CR$^4$R$^5$—, —CO—, —CR$^6$=CR$^7$, CR$^8$R$^9$—CR$^{10}$R$^{11}$ or SiR$^{12}$R$^{13}$;

$R^1$–$R^{13}$ are, identically or differently, H, a hydrocarbon radical having from 1 to 22 carbon atoms or Ar$^4$, where Ar$^4$, identical with or different from Ar$^1$, has the same meanings as Ar$^1$;

n=1, 2 or 3.

15 Claims, No Drawings

NITROGEN-CONTAINING POLYMERS AS ELECTROLUMINESCENT MATERIALS

There is a high industrial demand for large-area solid-state light sources for a number of applications, chiefly in the field of display elements, display screen technology and illumination. The requirements imposed on these light sources cannot currently be met entirely satisfactorily by any of the existing technologies.

As an alternative to conventional display and illumination elements such as incandescent lamps, gas discharge lamps and non-luminous liquid-crystal display elements use has been made for some time now of electroluminescent (EL) materials and devices such as light-emitting diodes (LED).

DE-A 25 45 784 (corresponds to U.S. Pat. No. 3,995,299) describes an electroluminescence device with a radiation source, which comprises a layer of an amorphous or predominantly amorphous polymer material having appreciable electrical charge mobility and low ionization potential, a strong electron donor, a strong electron acceptor and preferably at least one luminescent additive, electrical connections being provided through which an electric current can be passed through the thickness of the layer to excite radiation therefrom.

Polymer materials used include conjugated polymers such as poly(p-phenylenevinylene) (see e.g. WO-A 90/13148), as well as nonconjugated polymers (see e.g. I. Sokolik et al., J. Appl. Phys, 1993, 74, 3584), conjugated materials generally having the advantage of higher charge carrier mobility and consequently better efficiency and lower threshold voltages.

In addition to polymer-based devices, low molecular-weight organic electroluminescence devices have also been known for some time. Saito et al. (Appl. Phys. Lett. 1990, 56, 799) describe such devices containing triarylamine stilbenes as light-emitting layers.

Although good results have been achieved with these materials, the characteristic profile of these compounds still leaves substantial room for improvement.

Since, furthermore, the development of electroluminescent materials, especially those based on polymers, cannot yet in any way be regarded as complete, the manufacturers of illumination and display devices are interested in the most diverse electroluminescent materials for such devices.

One of the reasons for this is that only the interaction of the electroluminescent materials with the other components of the devices permits inferences regarding the quality, including that of the electroluminescent materials.

It was therefore an object of the present invention to provide novel electroluminescent materials which, when used in illumination or display devices, are suitable for improving the characteristic profile of these devices.

Surprisingly it has now been found that certain nitrogen-containing polymers are particularly suitable as electroluminescent materials.

Polymers containing triaryl units are known to some extent as photosensitive components for electrophotographic processes and as sensitizers for electrically photosensitive dyes (U.S. Pat. No. 4,323,203), but it is not possible to deduce therefrom that the novel polymers having a different structure might be suitable as electroluminescent materials.

The invention therefore relates to a polymer containing structural units of formula (I),

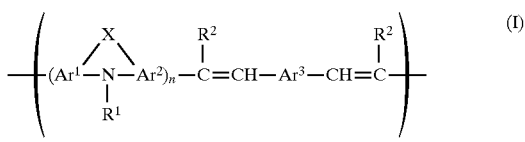

where the symbols and indices have the following meanings:

$Ar^1$, $Ar^2$, $Ar^3$ are, identically or differently, mono- and/or polynuclear and/or condensed aryl and/or heteroaryl groups which may or may not be linked via one or more bridges, preferably having from 4 to 400, particularly preferably from 4 to 100, especially preferably from 4 to 20 carbon atoms, which may or may not be substituted;

X is a single bond, —O—, —S—, —SO—, —SO$_2$, $NR^3$, —$CR^4R^5$—, —CO—, —$CR^6$=$CR^7$, $CR^8R^9$—$CR^{10}R^{11}$ or $SiR^{12}R1^{13}$;

$R^1$–$R^{13}$ are, identically or differently, H, a hydrocarbon radical which may or may not be substituted and may also contain hetero atoms, preferably O and/or F, having from 1 to 22 carbon atoms or $Ar^4$, where $Ar^4$, identical with or different from $Ar^1$, has the same meanings as $Ar^1$;

n is 1, 2 or 3, preferably 1 or 2, especially preferably 1.

Preference is given to polymers which consist of structural units of formula (I). The polymers according to the invention are distinguished, inter alia, by a low electroluminescence threshold voltage and a high efficiency. Moreover, they are particularly suitable as hole conductor materials.

Those materials are regarded as electroluminescent materials for the purpose of the invention which can be used as an active layer in an electroluminescence device. Active layer means that the layer is able, when an electric field is applied, to radiate light (light-emitting layer) and/or that it improves the injection and/or the transfer of the positive and/or negative charges (charge injection layer or charge transfer layer).

The invention therefore also relates to the use of a polymer containing structural units of formula (I) as an electroluminescent material, in particular as a hole conductor material, and to electroluminescent materials comprising one or more polymers containing structural units of formula (I).

The polymers according to the invention generally have from 2 to 1000, preferably from 3 to 500, particularly preferably from 4 to 300 repeat units.

Those polymers containing structural units of formula (I) are preferred in which the symbols and indices have the following meanings:

$Ar^1$, $Ar^2$, identically or differently, preferably identically, are

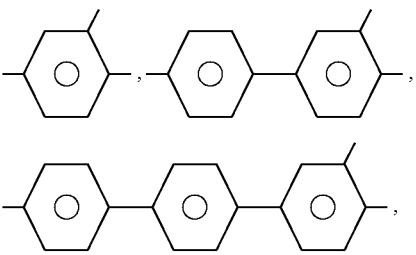

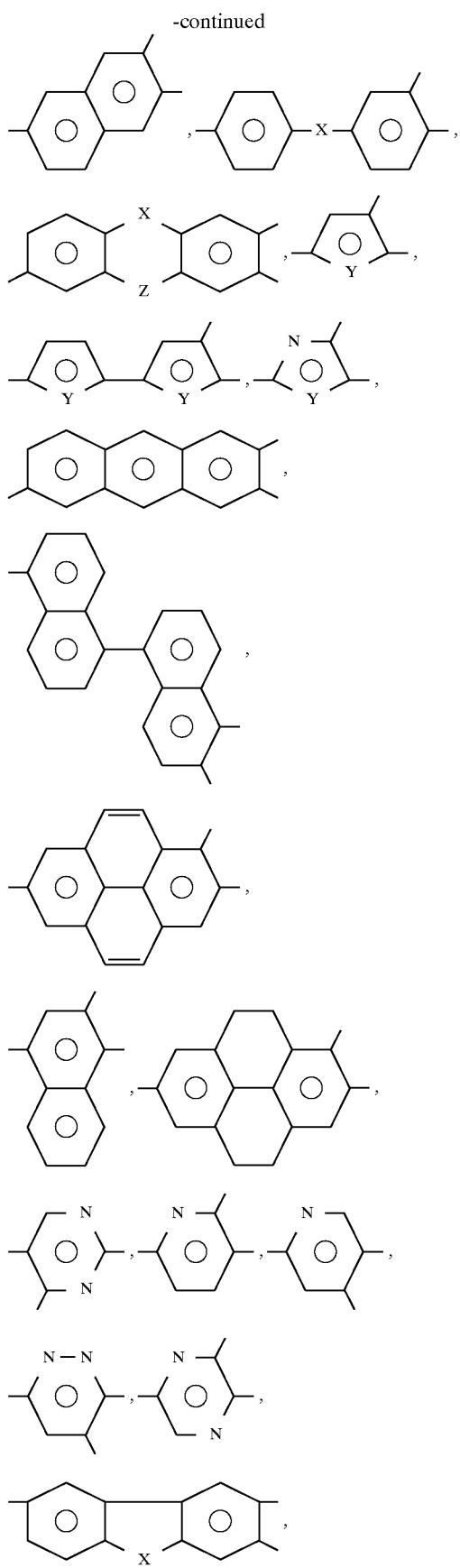

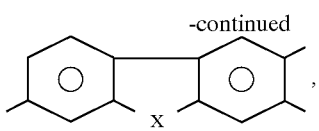

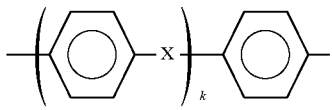

Ar³ identical with or different from Ar¹, Ar³, has the same meanings as Ar¹, only two of the three possible bonding sites being implemented in each $$-\!\!\left(\!\!\left\langle\bigcirc\right\rangle\!-\!X\!\right)_{\!k}\!\!\left\langle\bigcirc\right\rangle\!\!-$$

with k=1 to 20, preferably 1, 3 or 3;

Ar¹, Ar², Ar³ in this context may be substituted identically or differently with one or more radicals $R^{14}$;

X, Z identically or differently, are a single bond, —O—, —S—, —SO—, —SO$_2$—, —NR$^3$—, —CR$^4$R$^5$—, —CO—, —CR$^6$=CR$^7$, CR$^8$R$^9$—CR$^{10}$R$^{11}$ or SiR$^{12}$R$^{13}$;

Y: —O—, —S— or —NR$^3$—;

$R^1$–$R^{13}$ is H, a straight—chain or branched alkyl group having from 1 to 22 carbon atoms, one or two nonadjacent CH$_2$ groups optionally being replaced by —O—, —S—, —CO—, —CO—O—, —O—OC— or —Si(CH$_3$)$_2$—, a cycloalkyl group having from 3 to 10 carbon atoms or Ar$^4$, where Ar$^4$, identical with or different from Ar$^{1-3}$ has the same meanings as Ar$^{1-3}$, but only one of the three possible bonds is implemented, $R^4$–$R^{11}$ also being F, CF$_3$, O—CF$_3$ or CN;

$R^{14}$ is, identically or differently, H, an alkyl group having from 1 to 22, preferably from 1 to 12 carbon atoms, one or two nonadjacent CH$_2$ groups optionally being replaced by —O—, —S—, —CO—, —CO—O—, —O—OC— or —Si(CH$_3$)$_2$—, or is —CF$_3$, —Ph, —O—Ph, —S—Ph, —SO—Ph, —SO$_2$—Ph, F, Cl, Br, I or —CN;

n is 1, 2 or 3, preferably 1 or 2, particularly preferably 1.

Particularly preferred polymers containing structural units of formula (I) are those in which the symbols and indices have the following meanings:

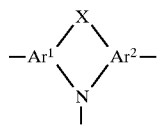

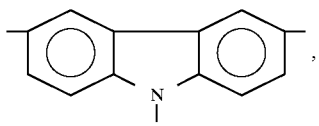

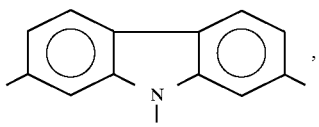

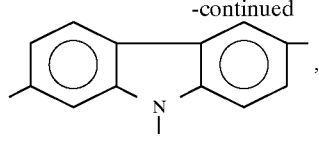,
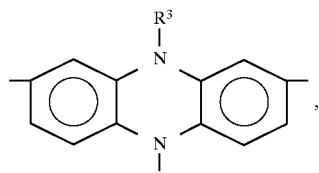,
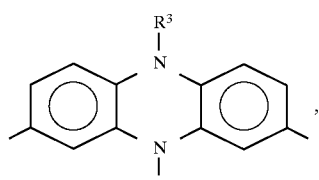,
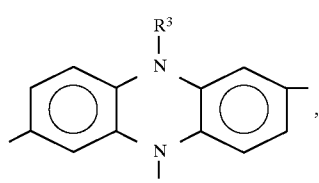,
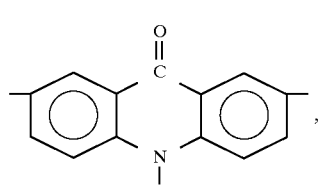,
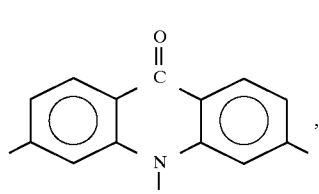,
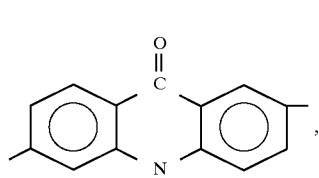,
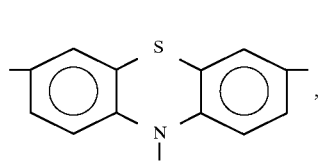,
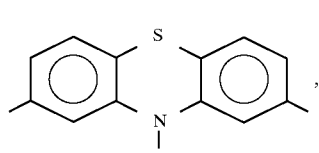,
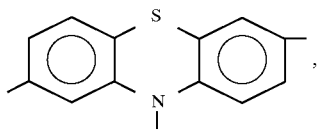,
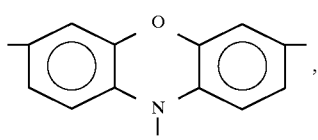,
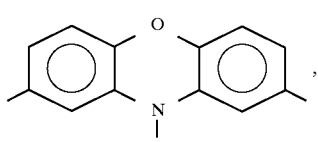,
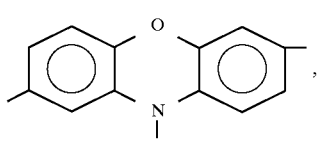,
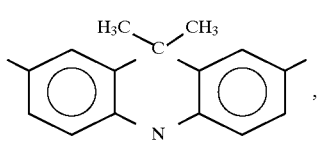,
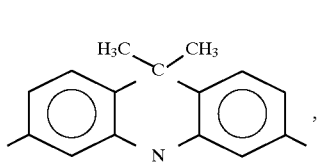,
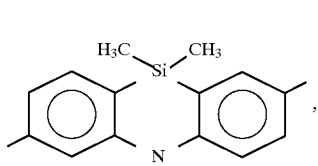,
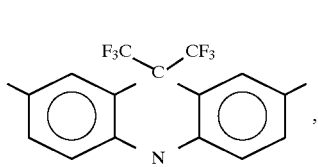,
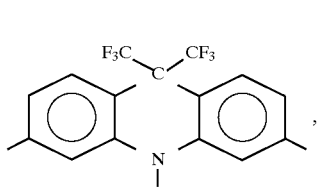, -continued

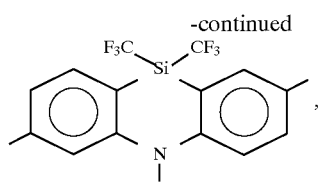

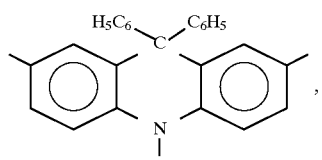

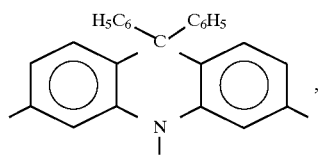

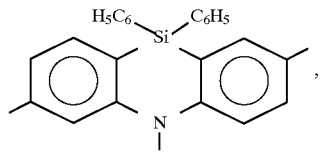

Ar³ is

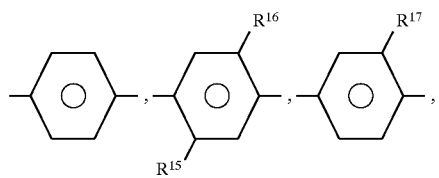

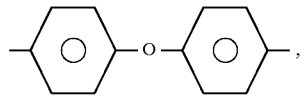

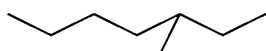

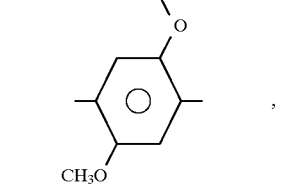

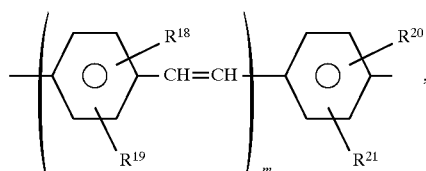

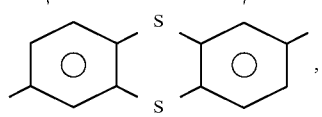

-continued

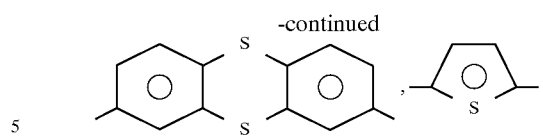

where m=1 . . . 20, preferably 1, 2 or 3, particularly preferably 1,

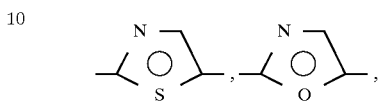

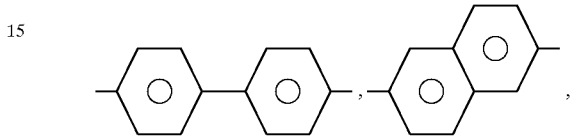

$R^1$, $R^2$, identical with or different from $Ar^3$, have the same meanings as $Ar^3$, only one of the two possible bonding sites to the polymer being implemented, however, or are

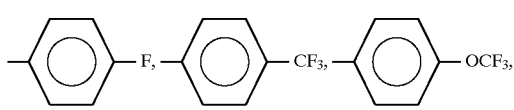

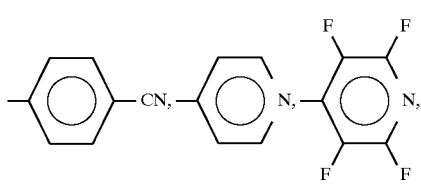

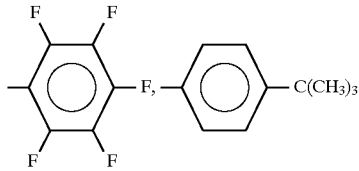

or are H, a straight-chain or branched alkyl group having from 1 to 12 carbon atoms, one or two nonadjacent $CH_2$ groups optionally being replaced by —O—, —S—, —CO—, —CO—O—, —O—OC— or —Si(CH$_3$)$_2$—, a cycloalkyl group having from 3 to 6 carbon atoms or, an aralkyl group having from 7 to 11 carbon atoms;

$R^{15}$–$R^{21}$ are, identically or differently, F, Cl, a straight-chain or branched alkyl or alkoxy group having from 1 to 22, preferably from 1 to 12 carbon atoms, $R^{18}$–$R^{21}$ may also be hydrogen.

Special preference is given to polymers containing structural units which have the formula (I) and in which $Ar^1$ and $Ar^2$ have identical meanings, and to polymers in which $R^2$ is H or $Ar^4$.

The polymers according to the invention may be homopolymers or copolymers. Copolymers contain different structural units of formula (I) and/or further structural units which may be conjugated or nonconjugated, for example 1,4-phenylene groups or α,ωalkylene groups.

The preparation of the novel polymers or polymers used according to the invention is expediently effected by condensing bisaldehydes or bisketones of formula (II)

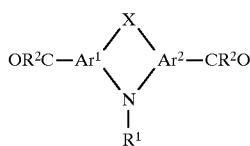

(II)

where $Ar^1$, $Ar^2$, $R^1$, $R^2$ and X have the meanings specified in formula (I) with organophosphorus compounds of formula (III)

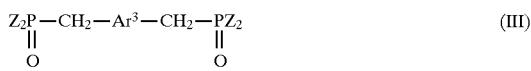

(III)

where $Ar^3$ has the meanings specified in formula (I) and Z is $C_1$–$C_{22}$-alkoxy, preferably ethoxy, or aryl radicals, preferably phenyl.

The condensation takes place by the action of a basic condensing agent, preferably of potassium t-butylate or sodium hydride.

The polycondensation is expediently carried out in such a way that the equimolar mixture of the starting components (II) and (III) in a solvent is introduced as an initial charge, into which, under an inert gas atmosphere and with stirring, preferably at least molar amounts of condensing agent are introduced in solution or suspension.

According to another version of the procedure, the condensing agent may also, on its own or together with the bisketone, be introduced as an initial charge in a solvent and the biphosphorus component may be added. Preferred solvents are benzene, toluene, xylene or dimethylformamide, the reaction temperature is preferably from 60° to 120° C. and the reaction time from 0.1 to 20, preferably from 0.1 to 5, particularly preferably from 0.1 to 1 hours. The reactions are almost quantitative.

The work-up can be carried out via the addition of water, optionally an acid such as acetic acid, and the separation of the organic reaction phases. For purification purposes, the condensation products obtained can be extracted, e.g. with alcohols or acetic acid, or precipitated from the solution in a solvent by means of a nonsolvent.

This preparation method is generally described, for example, in DD 84 272, Hörhold, H.-H.: Z. Chem. 12, 41—52 (1972); Hörhold, H.-H.; Bergmann, R.; Gottschaldt, J.; Drefahl, G.: Acta Chim. Acad. Sci. Hung. 81, 239–251; Hörhold, H.-H.; Bergmann, R.: Advances in the Chemistry of Thermally Stable Polymers, Warszawa, Polish Scientific Publishers, 29–48 (1977); Hörhold, H.-H.; Helbig, M.: Makromol. Chem., Macromol. Symp. 12, 229–258 (1987) and H örhold, H.-H.; Helbig, M.; Raabe, D.; Opfermann, J.; Scherf, U., Stockmann, R.; Weiβ, D.: Z. Chem. 27, 126 (1987).

The E/Z isomers formed in the Horner reaction, and isomers resulting from the possible position of the two double bonds with respect to one another (trans-trans-anti, trans-trans-syn, cis-trans-anti, cis-trans-syn, cis-cis-anti, cis-cis-syn) are all covered by the invention.

If different bisaldehydes or bisketones, respectively, and/or bisphosphonates are used, copolymers containing different structural units of formula (I) are obtained in a simple manner. In such copolymers the radicals $R^1$ in formula (I) may or may not even have different meanings. Furthermore, delayed addition of at least one of the comonomers provides the option of preparing block copolymers.

Smaller groups of polymers containing structural units of formula (I), in which $Ar^1$ has the meaning $Ar^5$—$Ar^5$, where $Ar^5$ is an electron-rich aromatic compound, preferably thiophen-2,5-ylene, which may or may not be substituted, may alternatively be polymerized oxidatively, e.g. with $FeCl_3$ (see inter alia P. Kovacic, N. B. Jones, Chem. Ber. 1987, 87, 357 to 379; M. Weda, T. Abe, H. Awano, Macromolecules 1992, 25, 5125) or electrochemically (see e.g. N. Saito, T. Kanbara, T. Sato, T. Yamamoto, Polym. Bull. 1993, 30, 285):

Polymerization by oxidation

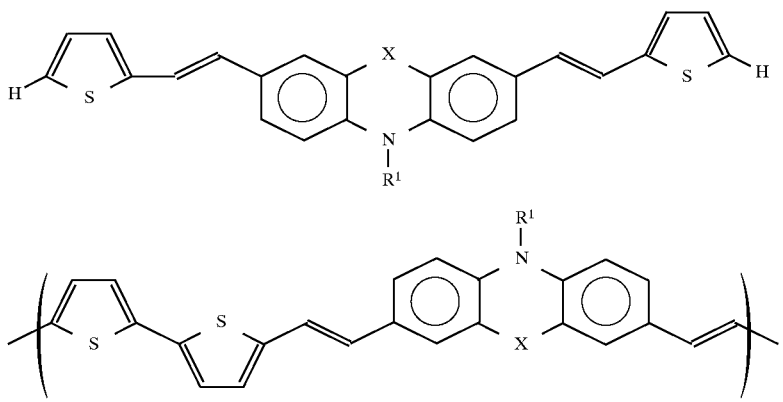

Equally it is possible for aromatic compounds to be coupled oxidatively under the conditions of the Scholl reaction:

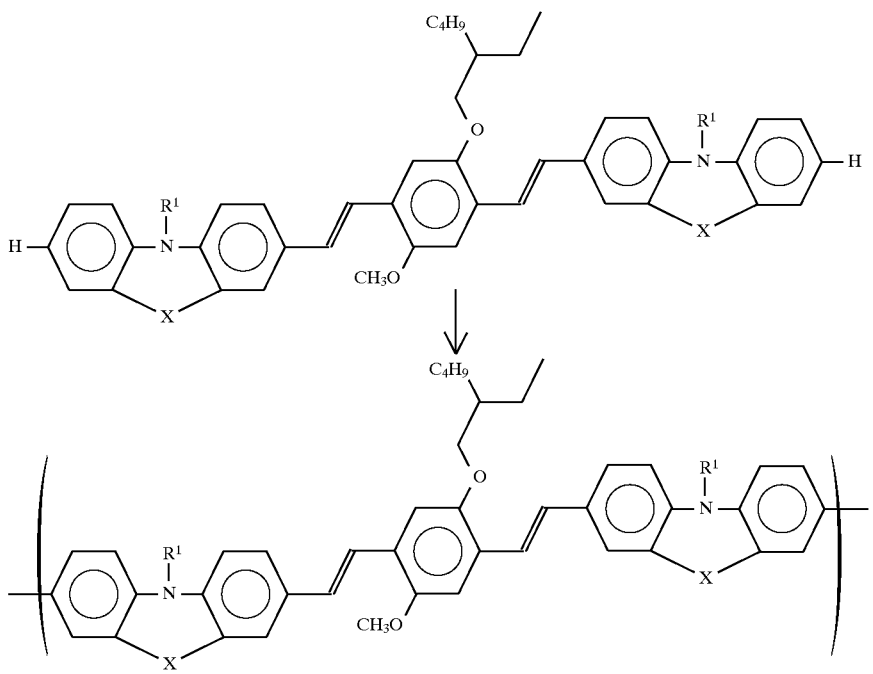

(see e.g. J. March, Advanced Organic Chemistry, 3rd Ed. p. 484 et seq., McGraw Hill and the literature cited there).

To control the molar mass during the polymerization it may be expedient to add monofunctional aldehydes or ketones in order to form defined endgroups, for example the commercially available N-ethyl-3-carbazolcarboxyaldehyde (from Aldrich, Milwaukee, U.S.A. ) or the following compound, which is readily obtained from 4-fluorobenzaldehyde.

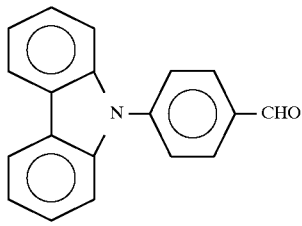

If two moles of a monofunctional aldehyde or a ketone are used together with one mole of an organophosphorus compound of formula (III), sesquimers of formula (Ia) are obtained,

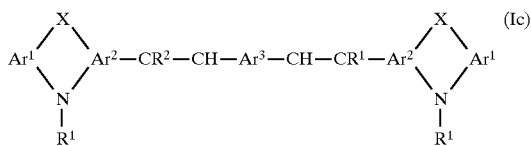 (Ic)

the symbols and indices having the same meanings and being subject to the same preferences as in formula (I).

Such compounds, particularly in a mixture with the polymers according to the invention, are likewise suitable as electroluminescent materials.

The polymerization of starting compounds having meta-substituted structural elements may give rise to macrocyclic compounds.

The polymers according to the invention or used according to the invention may therefore also be present in a mixture with said macrocyclic compounds, which does not interfere with the use as an electroluminescent material.

The preparation of the starting compounds (II) and (III) takes place according to methods known per se from the literature, as described in standard works on organic synthesis, e.g. Houben-Weyl, Methoden der Organischen Chemie, Georg-Thieme-Verlag, Stuttgart.

Said preparation takes place under reaction conditions which are known and are suitable for the abovementioned reactions. It may also make use of variants which are known per se and are not mentioned here in detail.

The bis(diphenylphosphane oxides) or bis(phosphonic acid esters) required as condensation components can be readily obtained, for example via the Michaelis-Arbusov reaction, from the corresponding bis(halomethyl) compounds with ethyl diphenylphosphinate $(C_6H_5)_2P-O-C_2H_5$ or with triethyl phosphite.

The synthesis of bisaldehydes of formula (II) can be carried out in accordance with various reaction types familiar to those skilled in the art.

Thus aldehydes can be obtained, for example, from bis-carboxylic acid derivatives by controlled reduction with reductants such as lithium tris-alkoxyalanates or $H_2/Pd$ ("Rosenmund reduction"):

(see e.g. Fuson in Patai, "The Chemistry of the Carbonyl Group", Vol. 1, p. 211–232, Interscience, New York 1966)

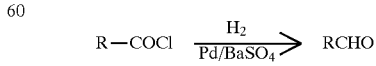

(see e.g. Tylander, "Catalytic Hydrogenation over Platinum Metals, p. 398–404, Academic Press, New York 1967).

From bis(chloromethyl) precursors it is possible to obtain bisaldehydes, for example via the Sommelet reaction:

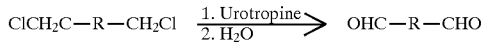

(see e.g. Angyal, Organic Reactions 1954, 8, 197).

Preferably, however, the underlying amines (IV) and (V)

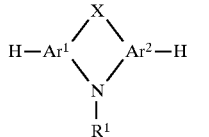

are subjected to electrophilic aromatic substitution.

Numerous methods for this are known, for example the Gattermann-Koch reaction:

(see e.g. Crounse, Organic Reactions 1949, 5, 290–300); the Gattermann reaction:

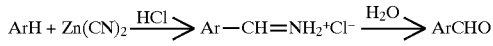

(see e.g. Truce, Organ. Reactions 1957, 9, 37–72); or the reaction of aromatic compounds with dichloromethyl methyl ether:

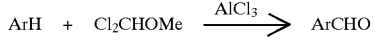

(see e.g. Rieche et al., Chem. Ber. 1960, 93, 88 or Lewin et al., Org. Prep. Proced. Int. 1978, 10, 201).

Preference, however, is given to the Vilsmeier reaction (likewise with DMF):

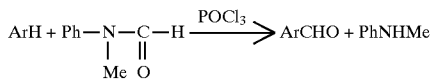

(see e.g. Jutz in Advances in Organic Chemistry, Vol. 9, Part 1, pp. 225–342, Böhme, Viche Eds. Interscience, New York 1976, or Jackson, J. Am. Chem. Soc. 1981, 103, 533).

If $R^1$ in formula (I) is not hydrogen, bisketones are used as the starting materials.

These may be prepared, for example, via the above-described Vilsmeier reaction, if the amide used is not formamide.

Bisketones may also be prepared by the Friedel-Crafts acylation:

(see, for example, Olah, Friedel-Crafts and Related Reactions, Vol. 2, 979–1047, Interscience, New York 1963–65); or via a Grignard reaction with cyanoarylene:

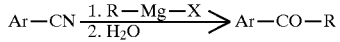

(see, e.g. Kharasch and Rainmuth, Grignard Reactions of Nonmetallic Substances, p. 767–845, Prentice Hall, Eagle-wood Cliffs, N.J. 1954). The starting compounds for bisaldehydes and bisketones are the amines (IV). They can be prepared in accordance with known methods familiar to those skilled in the art.

Such methods are described, for example, in A. R. Katritzky and I. M. Lagowski, The Principles of Heterocyclic Chemistry, Methuen, London 1967, or in the corresponding volumes of the series "The chemistry of Heterocyclic Compounds" by A. Weissberger and E. C. Taylor (editors).

Thus the amines of formula (IV) can be obtained, for example, from the corresponding diiodo compounds:

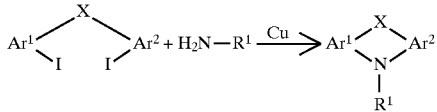

Many of the compounds are also commercially available, for example: carbazole, N-methylcarbazole, N-phenylcarbazole, N-biphenylylcarbazole, dihydrophenazine, acridinone, phenoxazine (dibenzoxazine), phenothiazine (dibenzothiazine), all from Aldrich, Steinheim, Germany or 9,9-diphenyl-9,10-dihydro-9-silaacridine and 9,9-dibenzyl-9,10-dihydro-9-silaacridine (from Salor, Steinheim, Germany).

For the polymers according to the invention to be used as electroluminescent materials, they are generally applied to a substrate in the form of a film by known methods familiar to those skilled in the art, such as dipping or spin-coating.

The invention therefore also relates to a method for preparing an electroluminescent material which comprises a) condensing an organophosphorus compound of formula (III)

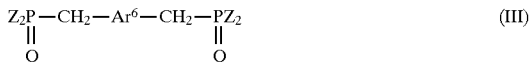

with a bisaldehyde or bisketone of formula (II)

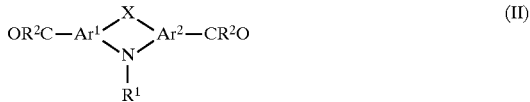

in the presence of a basic condensing agent to produce a polymer containing structural units of formula (I),

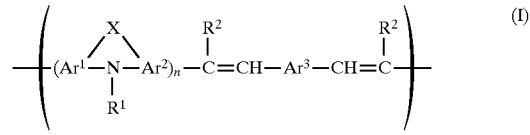

where the symbols and indices have the following meanings:

$Ar^1$, $Ar^2$, $Ar^3$ are, identically or differently, mono-and/or polynuclear and/or condensed aryl and/or heteroaryl groups which may or may not be linked via one or more bridges, preferably via one bridge, preferably having from 4 to 400, particularly preferably from 4 to 100, especially preferably from 4 to 20 carbon atoms, which may or may not be substituted;

X is a single bond, —O—, —S—, —SO—, —SO$_2$, NR$^3$, —CR$^4$R$^5$—, —CO—, —CR$^6$═CR$^7$, CR$^8$R$^9$—CR$^{10}$R$^{11}$ or SiR$^{12}$R$^{13}$;

$R^1$–$R^{13}$ are, identically or differently, H, a hydrocarbon radical having from 1 to 22 carbon atoms or $Ar^4$, where $Ar^4$ can have the same meanings as $Ar^1$;

n=1, 2 or 3, preferably 1 or 2, particularly preferably 1, and b) applying the resulting polymer which contains structural units of formula (I) as a film to a substrate which may or may not already contain other layers.

The invention further relates to an electroluminescence device comprising one or more active layers, at least one of said active layers containing one or more polymers according to the invention. The active layer may, for example, be a light-emitting layer and/or a transfer layer and/or a charge injection layer. Preferably it is a light-emitting layer or a hole conductor layer.

The general structure of such electroluminescence devices is described, for example, in U.S. Pat. No. 4,539,507 and U.S. Pat. No. 5,151,629. Electroluminescence devices which contain polymers are described, for example, in WO-A 90/13148 or EP-A 0,443,861.

They usually contain an electroluminescent layer between a cathode and an anode, at least one of the electrodes being transparent. Additionally, an electron injection and/or electron transfer layer may be sandwiched between the electroluminescent layer and the cathode, and/or a hole injection and/or hole transfer layer may be sandwiched between the electroluminescent layer and the anode. Metals and metal alloys, e.g. Ca, Mg, Al, In or Mg/Ag may serve as the cathode. Metals, e.g. Au or other metallically conductive materials, e.g. ITO (indium oxide/tin oxide) on a transparent substrate, e.g. made of glass or a transparent polymer, may serve as the anode.

During operation, the cathode is placed at a negative potential with respect to the anode. In the process, electrons are injected from the cathode into the electron injection layer/electron transfer layer or directly into the light-emitting layer. At the same time, holes are injected from the anode into the hole injection layer/hole transfer layer or directly into the light-emitting layer.

Under the influence of the voltage applied, the injected charge carriers move towards one another through the active layers. As a result, electron/hole pairs are produced at the interface between charge transfer layer and light-emitting layer or within the light-emitting layer, which recombine, emitting light in the process.

The color of the emitted light can be varied via the materials employed as the light-emitting layer. Electroluminescence devices are used, e.g., as luminous display elements such as pilot lamps, alphanumeric displays, information signs, and in optoelectronic couplers.

The invention is illustrated in more detail by the examples, but is not intended to be limited thereby.

Tg: Glass transition temperature, measured by means of differential scanning calorimetry (DSC)

$M_n$: Number-average molecular weight

VPO: Vapor pressure osmometry (see, for example, Cherdron, Kern, Braun, Praktikum der Makromolekularen Chemie (Practical Macromolecular Chemistry )

GPC: Gel permeation chromatography, polystyrene being the standard

EXAMPLES

Example 1

3,6-Dibenzoyl-9-methylcarbazole 3,6-Dibenzoyl-9-methylcarbazole (4): 67.0 g (0.37 mol) of 9-methylcarbazole were dissolved in 400 ml of dry dichloroethane, to which 105.0 g (0.79 mol) of $AlCl_3$ were added. 104.0 g (0.74 mol) of benzoyl chloride were added dropwise with stirring and cooling with ice. Stirring was continued for another 3 hours at room temperature, and the reaction mixture was then decomposed with ice and hydrochloric acid and the organic phase was washed to neutrality with water and $NaHCO_3$ solution. The remaining water was removed by azeotropic distillation. The dichloroethane solution was concentrated, whereupon the diketone crystallized out. It was recrystallized once more from dichloroethane; m.p. 222° C.; (Lit. [16]): m.p. 2190° C.), colorless crystals. Yield: 114.2 g (79.3%).

$C_{27}H_{19}NO_2$ Calc. C 83.27 H 4.92 N 3.60 (389.5) Obs. C 83.45 H 4.86 N 3.50

Example 2

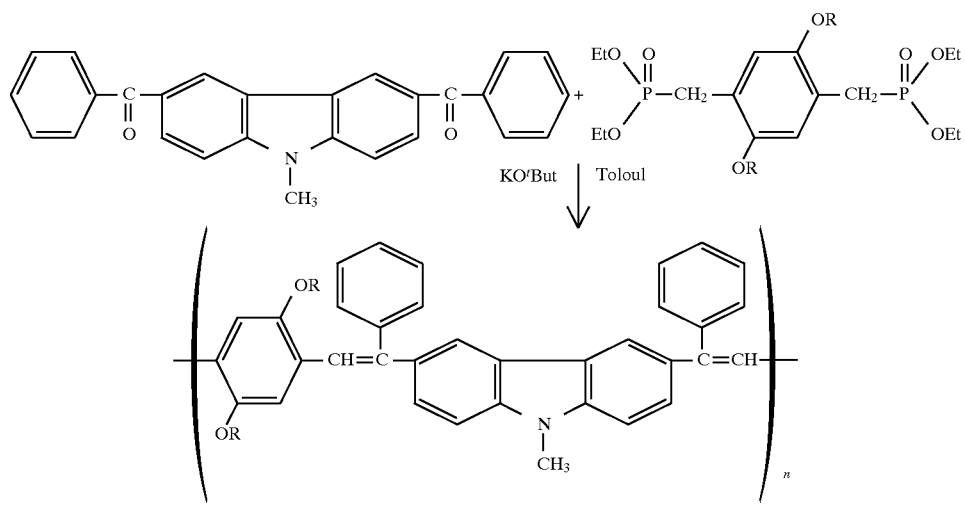

R = n-$C_8H_{17}$

Poly(9-methylcarbazole-3, 6-diyl-1-phenyl-1,2-ethylene2, 5-dioctoxy-1,4-phenylene-2-phenyl-1,2-ethylene)

| | |
|---|---|
| 3,6-dibenzoyl-9-methylcarbazole | (389.1) = 1.83 g (0.0047 mol) |
| 2,5-dioctoxy-p-xylene-bis-(diethyl phosphate) | (634.7) = 3.00 g (0.0047 mol) |
| Potassium t-butylate | (112.2) = 2.00 g (0.0178 mol) |

Solvent: toluene

The diketone and the bisphosphonate are dissolved in a small amount of boiling toluene, with stirring and under an inert gas, and solid potassium t-butylate is added all at once. The mixture boils up violently and abruptly becomes viscous. After 10 minutes, about 20 ml of toluene are added to facilitate stirring. Stirring continues for another two hours, after which the solvent is stripped off, the residue is taken up in chloroform, followed by precipitation in isopropanol. The yellow floccules obtained are extracted with methanol for 5 hours and reprecipitated once more (chloroform/methanol). After drying, a yellow powder is obtained with a yield of 68%.

analytical data:

glass transition temperature Tg: 90° C.

fluorescence $\lambda_{max.em}$=505 nm $\theta$=30%

UV/VIS=$\lambda_{max.abs}$=400.8 nm log $\epsilon$=4.5

$E^{ox-}1$=0.91V vs Ag/AgCl

Mn (VPO)=4500

Mn (GPC)=5200 Mw (GPC)=11,300

Example 3

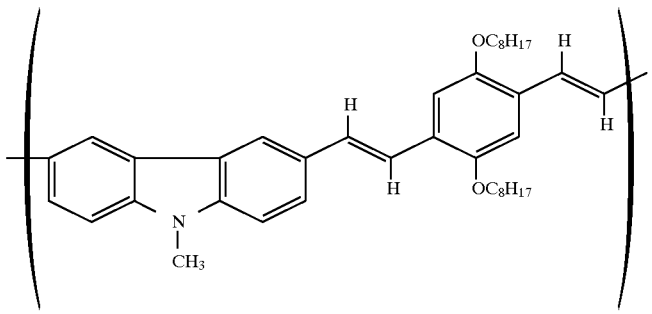

The starting material 3,6-diformyl-N-methyl-carbazole was obtained by a Vilsmeier reaction. The further synthesis was carried out in a manner similar to Example 2.

$M_w$>10,000

$\phi$PL 75%, the polymer is soluble in chlorobenzene and sparingly soluble in chloroform.

Example 4

Electroluminescence device

A 2 wt % solution of the polymer from Example 2 in chlorobenzene is applied, under nitrogen, to a glass carrier coated with ITO (indium tin oxide) (patterned, 2 mm wide strips) by spin-coating at 500 rpm. The glass carrier is transferred via a lock, the inert gas atmosphere being maintained, into a high-vacuum vapor deposition system. At $2\times10^{-5}$ mbar, Ca strips (2 mm wide, 230 nm thick) are vapor-deposited transversely to the ITO strips onto the polymer layer, a mask being used. The device thus obtained, ITO/polymer/Ca, is placed in a sample holder and the electrodes are connected to a current source via spring contacts, an ITO strip being connected to the positive terminal and a Ca strip being connected to the negative terminal. If a sufficiently high voltage is applied, green electroluminescence is observed on the corresponding matrix element.

Threshold voltage: 7.0 v

Max. efficiency: 0.032%

Max. luminance 120 Cd/m$^2$ at 13 v and 7 mA/4 mm$^2$

We claim:

1. A polymer containing structural units of formula (I),

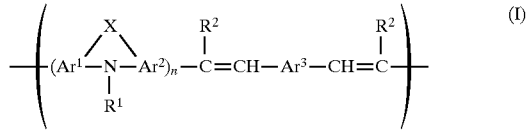

where the symbols and indices have the following meanings:

Ar$^1$, Ar$^2$, Ar$^3$ are, identically or differently, mono- and/or and/or polynuclear and/or condensed aryl and/or heteroaryl groups which is optionally linked via at least one bridges carbon atoms, which is optionally substituted;

X is a single bond, —O—, —S—, —SO—, —SO$_2$, NR$^3$, —CR$^4$R$^5$—, —CO—, —CR$^6$=CR$^7$, CR$^8$R$^9$—CR$^{10}$R$^{11}$ or SiR$^{12}$R$^{13}$;

R$^1$–R$^{13}$ are, identically or differently, H, a hydrocarbon radical which is optionally substituted and optionally containing hetero atoms, having from 1 to 22 carbon atoms or Ar$^4$, where Ar$^4$, identical with or different from Ar$^1$, has the same meaning as Ar$^1$;

n is 1, 2 or 3.

2. The polymer as claimed in claim 1, which consists of structural units of formula (I).

3. The polymer as claimed in claim 1, which comprises from 2 to 1000 repeating units.

4. The polymer as claimed in claim 1 which is in the form of a copolymer.

5. The polymer as claimed in claim 4, which comprises different structural units of formula (I).

6. The polymer as claimed in claim 1, wherein the symbols and indices in formula (I) have the following meanings:

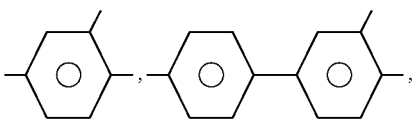

-continued

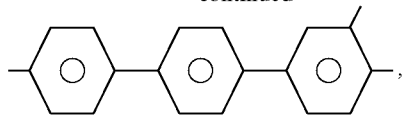

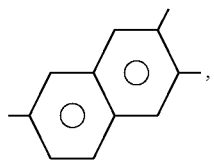

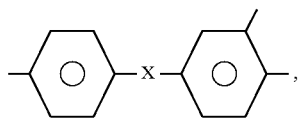

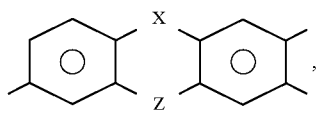

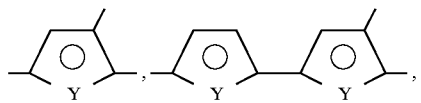

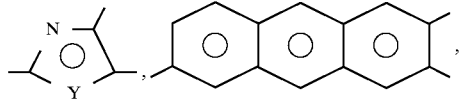

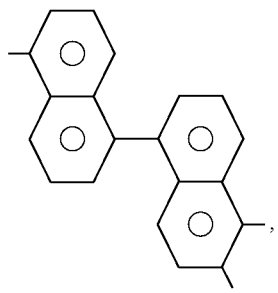

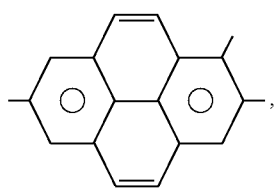

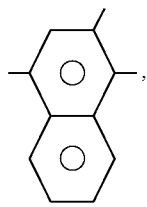

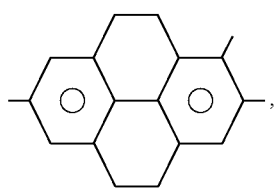

-continued

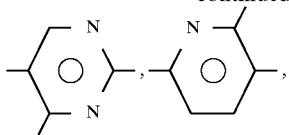

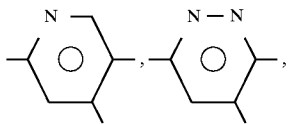

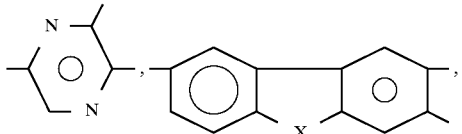

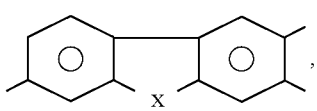

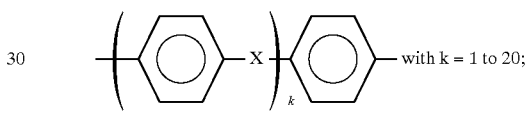

$Ar^3$, identical with or different from $Ar^1$, $Ar^3$, has the same meanings as $Ar^1$, only two of the three possible bonding sites being implemented in each case, or is $$\left(\!\!\left\langle\!\!\bigcirc\!\!\right\rangle\!-\!X\!\right)_{\!\!k}\!\!\left\langle\!\!\bigcirc\!\!\right\rangle\!\!-\text{ with } k = 1 \text{ to } 20;$$

$Ar^1$, $Ar^2$, $Ar^3$ in this context may be substituted identically or differently with at least one radicals $R^{14}$;

X, Z identically or differently, are single bond, —O—, —S—, —SO—, —SO$_2$—, NR$^3$, —CR$^4$R$^5$—, —CO—, —CR$^6$=CR$^7$, CR$^8$R$^9$—CR$^{10}$R$^{11}$ or SiR$^{12}$R$^{13}$;

Y: —O—, —S— or —NR$^3$—;

$R^1$–$R^{13}$ is H, a straight-chain or branched alkyl group having from 1 to 22 carbon atoms, one or two nonadjacent CH$_2$ groups optionally being replaced by —O—, —S—, —CO—, —CO—O—, —O—OC— or —Si(CH$_3$)$_2$—, a cycloalkyl group having from 3 to 10 carbon atoms or Ar$^4$, where Ar$^4$, identical with or different from Ar$^{1-3}$ has the same meanings as Ar$^{1-3}$, but only one of the three possible bonds is implemented, $R^4$–$R^{11}$ also being F, CF$_3$, O—CF$_3$ or CN;

$R^{14}$ is, identically or differently, H, an alkyl group having from 1 to 22 carbon atoms, one or two nonadjacent CH$_2$ groups optionally being replaced by —O—, —S—, —CO—, —CO—O—, —O—OC— or —Si(CH$_3$)$_2$—, —CF$_3$, —Ph, —O—Ph, —S—Ph, —SO—Ph, —SO$_2$—Ph, F, Cl, Br, I or —CN;

n is 1, 2 or 3.

7. The polymer as claimed in claim 1, wherein the symbols and indices in formula (I) have the following meanings:

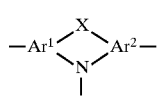

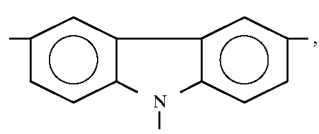
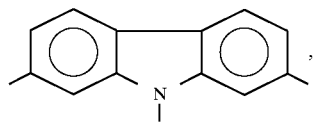
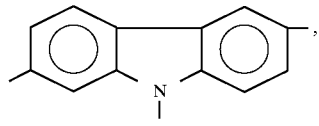
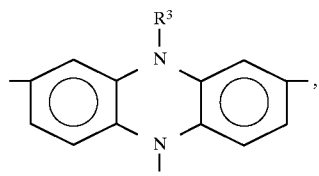
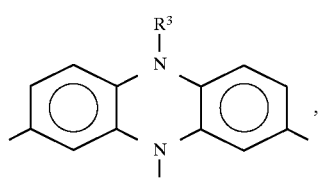
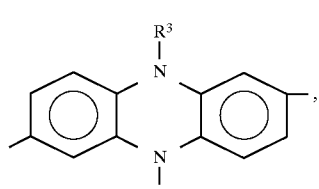
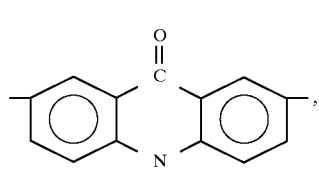
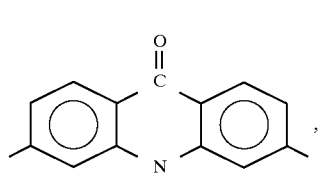
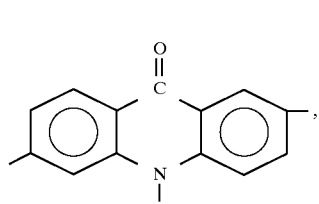
-continued
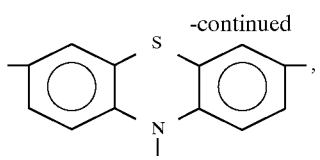
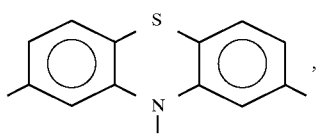
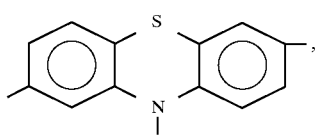
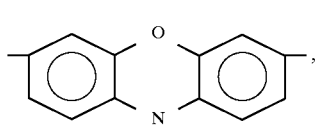
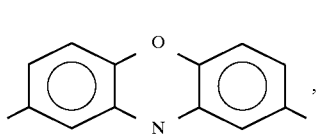
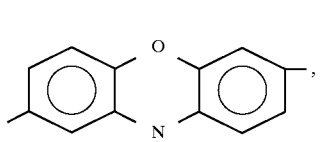
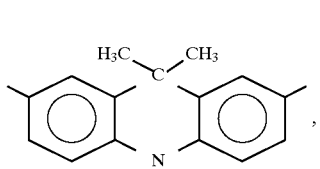
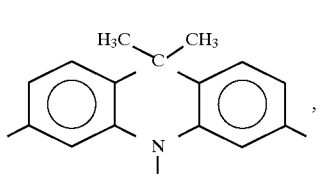
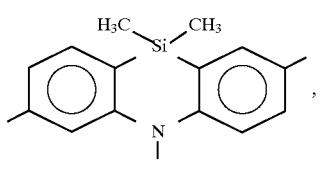
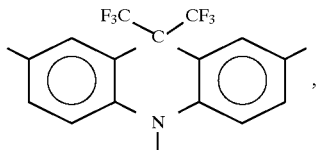

-continued

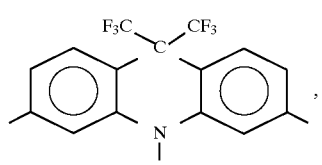

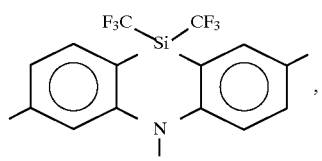

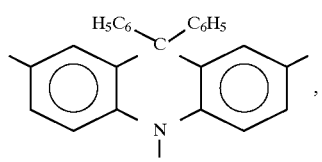

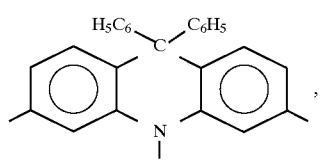

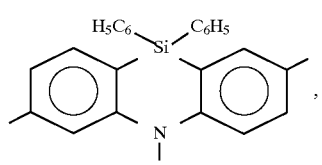

Ar³ is

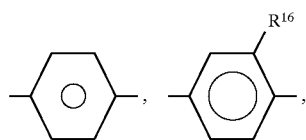

-continued

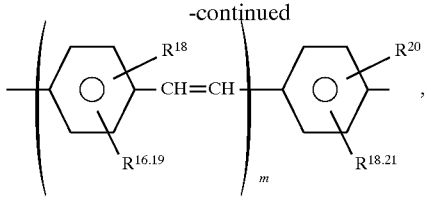

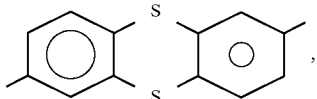

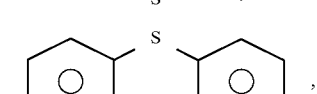

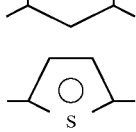

where m=1 . . . 20,

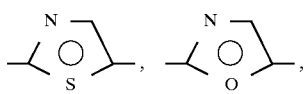

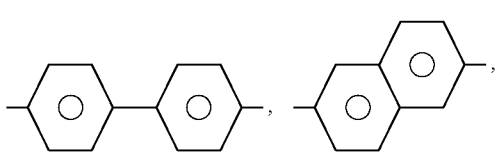

R¹, R², identical with or different from Ar³, have the same meanings as Ar³, only one of the two possible bonding sites to the polymer being implemented or are

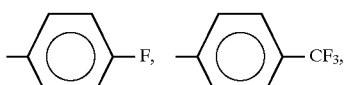

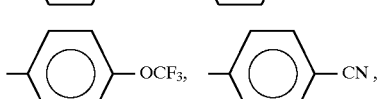

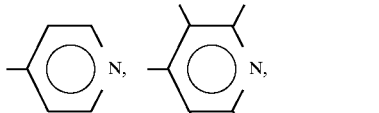

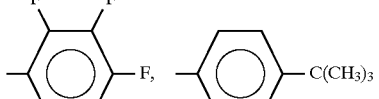

or is H, a straight-chain or branched alkyl group having from 1 to 12 carbon atoms, one or two nonadjacent $CH_2$ groups optionally being replaced by —O—, —S—, —CO—, —CO—O—, —O—OC— or —Si($CH_3$)$_2$—, a cycloalkyl group having from 3 to 6 carbon atoms or an aralkyl group having from 7 to 11 carbon atoms;

$R^{15}$–$R^{21}$ are, identically or differently, F, Cl, a straight-chain or branched alkyl or alkoxy group having from 1 to 22 carbon atoms, $R^{18}$–$R^{21}$ is optionally hydrogen.

8. The polymer as claimed in claim 1, wherein $Ar^1$ and $Ar^2$ are identical.

9. A method for preparing a polymer as claimed in claim 1, wherein bisaldehydes or bisketones of formula (II)

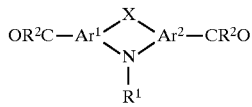
(II)

where $Ar^1$, $Ar^2$, $R^1$, $R^2$ and X have the meanings specified in formula (I) are condensed with organophosphorus compounds of formula (III)

(III)

where $Ar^3$ has the meanings specified in formula (I) and Z is $C_1$–$C_{22}$-alkoxy.

10. An electroluminescent material comprising one or more polymers as claimed in claim 1.

11. A method for preparing an electroluminescent material as claimed in claim 10, which comprises a) condensing an organophosphorus compound of formula (III)

(III)

with a bisaldehyde or bisketone of formula (II)

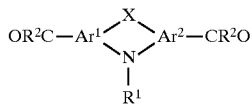
(II)

in the presence of a basic condensing agent to produce a polymer containing structural units of formula (I),

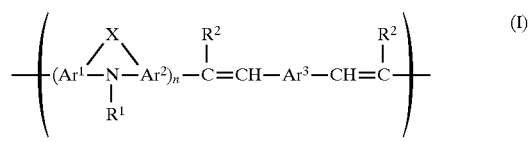
(I)

where the symbols and indices have the following meanings:

$Ar^1$, $Ar^2$, $Ar^3$ are, identically or differently, mono- and/or polynuclear and/or condensed aryl and/or heteroaryl groups which is optionally linked via at least one bridges carbon atoms, which is optionally substituted;

X is a single bond, —O—, —S—, —SO—, —$SO_2$, $NR^3$, —$CR^4R^5$—, —CO—, —$CR^6$=$CR^7$, $CR^8R^9$—$CR^{10}R^{11}$ or $SiR^{12}R^{13}$;

$R^1$–$R^{13}$ are, identically or differently, H, a hydrocarbon radical having from 1 to 22 carbon atoms or $Ar^4$, where $Ar^4$, identical with or different from $Ar^1$, has the same meaning as $Ar^1$;

n is 1, 2 or 3, and b) applying the resulting polymer which contains structural units of formula (I) as a film to a substrate which optionally already contain other layers.

12. Electroluminescence device comprising at least one active layers, at least one of said active layers containing at least one polymers as claimed in claim 1.

13. The polymer as claimed in claim 1, wherein the hetero atoms are O and/or F.

14. The polymer as claimed in claim 7, wherein m is 1, 2 or 3.

15. A method for using the polymer of claim 1 as an electroluminescent material.

* * * * *